(12) United States Patent
Tahara et al.

(10) Patent No.: US 10,624,538 B2
(45) Date of Patent: Apr. 21, 2020

(54) EYELID DETECTION DEVICE, DROWSINESS DETERMINATION DEVICE, AND EYELID DETECTION METHOD

(71) Applicant: Mitsubishi Electric Corporation, Tokyo (JP)

(72) Inventors: Natsuki Tahara, Tokyo (JP); Yudai Nakamura, Tokyo (JP); Takashi Hirano, Tokyo (JP); Masanobu Osawa, Tokyo (JP)

(73) Assignee: MITSUBISHI ELECTRIC CORPORATION, Tokyo (JP)

( * ) Notice: Subject to any disclaimer, the term of this patent is extended or adjusted under 35 U.S.C. 154(b) by 0 days.

(21) Appl. No.: 16/338,675

(22) PCT Filed: Jan. 17, 2017

(86) PCT No.: PCT/JP2017/001361
§ 371 (c)(1),
(2) Date: Apr. 1, 2019

(87) PCT Pub. No.: WO2018/134875
PCT Pub. Date: Jul. 26, 2018

(65) Prior Publication Data
US 2019/0320890 A1 Oct. 24, 2019

(51) Int. Cl.
*G08B 23/00* (2006.01)
*A61B 3/113* (2006.01)
(Continued)

(52) U.S. Cl.
CPC ............... *A61B 3/113* (2013.01); *A61B 5/18* (2013.01); *G06K 9/00845* (2013.01);
(Continued)

(58) Field of Classification Search
CPC .......... A61B 3/113; A61B 5/18; A61B 5/1103; G06K 9/00845; B60K 28/06; G06T 7/60
(Continued)

(56) References Cited

U.S. PATENT DOCUMENTS

| 5,859,686 A * | 1/1999 | Aboutalib | A61B 3/113 |
| | | | 351/209 |
| 2014/0112580 A1* | 4/2014 | Hanita | G06T 1/00 |
| | | | 382/165 |

(Continued)

FOREIGN PATENT DOCUMENTS

| JP | 2000-137792 A | 5/2000 |
| WO | WO 2012/144020 A1 | 10/2012 |

OTHER PUBLICATIONS

International Search Report for PCT/JP2017/001361 (PCT/ISA/210) dated Feb. 21, 2017.

*Primary Examiner* — Tanmay K Shah
(74) *Attorney, Agent, or Firm* — Birch, Stewart, Kolasch & Birch, LLP

(57) ABSTRACT

An eyelid detection device includes a face feature point detecting unit for detecting outer and inner eye corners as face feature points from a captured image, an eye region detecting unit for detecting an eye region including both an upper eyelid area and an eye area from the captured image on the basis of the face feature points, and an upper eyelid detecting unit for, for each of a plurality of divided areas into which the eye region is divided, detecting the boundary between the upper eyelid area and the eye area on the basis of the pattern of arrangement of the intensity values of pixels aligned in the divided region, and for connecting the boundary detected for each of the divided regions, to determine an upper eyelid.

14 Claims, 11 Drawing Sheets

(51) Int. Cl.
    *A61B 5/18*     (2006.01)
    *G06K 9/00*     (2006.01)
    *A61B 5/11*     (2006.01)
    *B60K 28/06*     (2006.01)
    *G06T 7/60*     (2017.01)

(52) U.S. Cl.
    CPC ............ *A61B 5/1103* (2013.01); *B60K 28/06* (2013.01); *G06T 7/60* (2013.01)

(58) Field of Classification Search
    USPC .......................................................... 340/575
    See application file for complete search history.

(56) References Cited

U.S. PATENT DOCUMENTS

| | | | |
|---|---|---|---|
| 2014/0161317 A1* | 6/2014 | Hiramaki | G06K 9/0061 382/103 |
| 2014/0205149 A1* | 7/2014 | Nakamura | A61B 5/163 382/103 |
| 2016/0171321 A1* | 6/2016 | Ohsuga | A61B 5/168 345/419 |
| 2017/0080947 A1* | 3/2017 | Boos | A61B 5/7278 |

\* cited by examiner

EYELID DETECTION DEVICE, DROWSINESS DETERMINATION DEVICE, AND EYELID DETECTION METHOD

TECHNICAL FIELD

The present disclosure relates to eyelid detection devices and eyelid detection methods for detecting an eyelid, and drowsiness determination devices for determining drowsiness on the basis of the detected eyelid.

BACKGROUND ART

Driver monitoring devices for detecting the degree (hereinafter referred to as "degree of eye openness" or "eye openness degree") to which an eye of the driver of a vehicle is open are known. A conventional driver monitoring device extracts an eye region from a captured image of the face of a driver, and performs both edge detection and curve detection on an image of the eye region, thereby detecting upper and lower eyelids (for example, see Patent Literature 1).

CITATION LIST

Patent Literature

Patent Literature 1: JP 2000-137792 A

SUMMARY OF INVENTION

Technical Problem

Because the conventional driver monitoring device is configured as described above, it involves a problem in that it detects a boundary between a makeup area and a no-makeup area from a captured image of a driver wearing a lot of makeup, such as thick eyeliner or dark eyeshadow, on his or her eyelids to erroneously detect the boundary as an upper eyelid.

Furthermore, the conventional driver monitoring device involves another problem in that it detects a boundary between a shadow area and a non-shadow area from a captured image of a driver whose face has chiseled features, which are likely to cause shadows around his or her eyes, to erroneously detect the boundary as an upper eyelid.

When erroneously detecting an upper eyelid, the driver monitoring device erroneously determines that the eyes of a driver are open even though the eyes of the driver are actually closed, and cannot calculate a correct degree of eye openness, so that a drowsiness determining process does not operate properly.

Embodiments of the present disclosure are made in order to solve the above-mentioned problems. An object of the embodiments of the present disclosure is to detect an upper eyelid of a person having makeup or a shadow around his or her eyes with a high degree of accuracy.

Solution to Problem

An eyelid detection device according to the present disclosure includes: a face feature point detecting unit for detecting outer and inner eye corners as face feature points from a captured image; an eye region detecting unit for detecting an eye region including both an upper eyelid area and an eye area from the captured image on a basis of the face feature points; and an upper eyelid detecting unit for detecting, for each of a plurality of divided areas into which the eye region is divided, a boundary between the upper eyelid area and the eye area on a basis of a pattern of arrangement of intensity values of pixels aligned in a divided area, and for connecting the boundaries each detected in the divided area to determine an upper eyelid.

Advantageous Effects of Invention

According to the present disclosure, because for each of the plurality of divided areas into which the eye region is divided, the boundary between the upper eyelid area and the eye area is detected on the basis of the pattern of arrangement of the intensity values of the pixels aligned in the divided region, and the boundaries each detected in the divided area are connected to determine an upper eyelid, an upper eyelid of a person having makeup or a shadow around his or her eyes can be detected with a high degree of accuracy.

DESCRIPTION OF EMBODIMENTS

Hereafter, in order to explain the present invention in greater detail, embodiments for carrying out the present invention are described with reference to the accompanying drawings.

Embodiment 1

Figure 1:
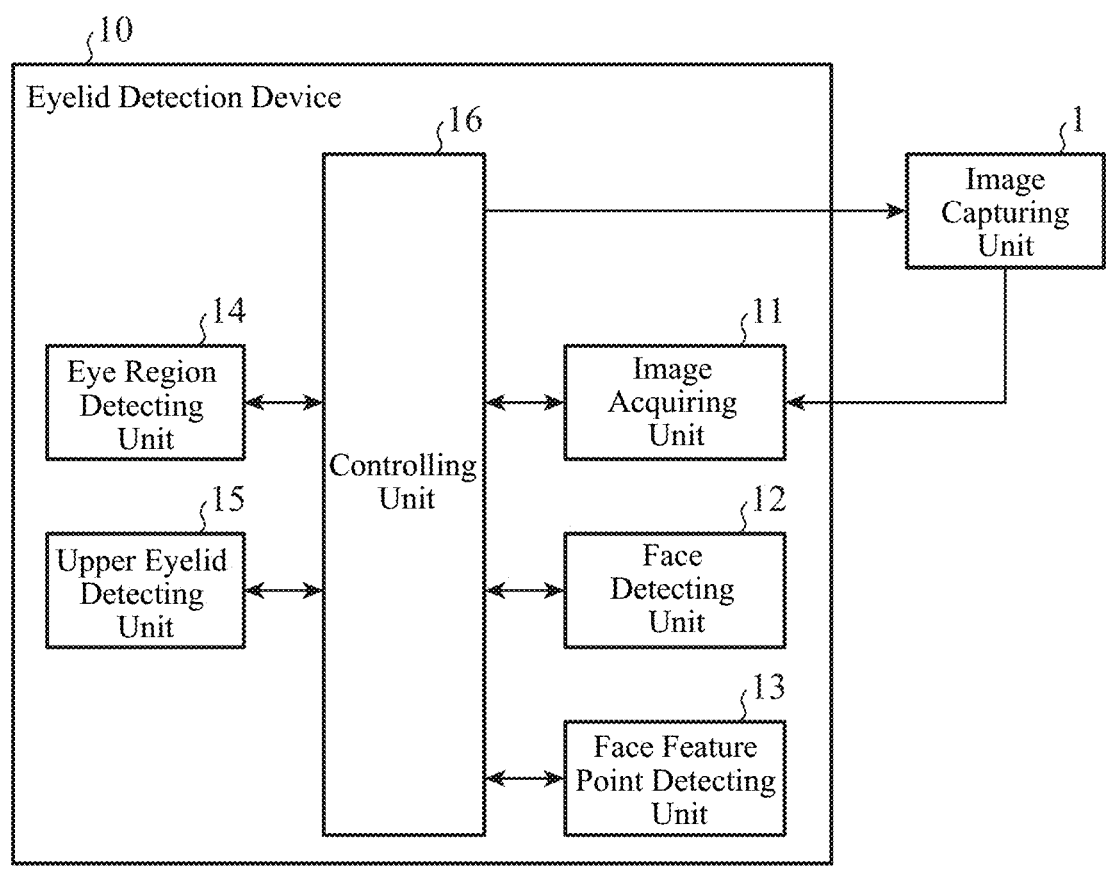
FIG. 1 is a block diagram showing a configuration example of an eyelid detection device according to Embodiment 1 of the present disclosure.

FIG. 1 is a block diagram showing a configuration example of an eyelid detection device 10 according to Embodiment 1 of the present disclosure. The eyelid detection device 10 shown in FIG. 1 includes an image acquiring unit 11, a face detecting unit 12, a face feature point detecting unit 13, an eye region detecting unit 14, an upper eyelid detecting unit 15, and a controlling unit 16. Moreover, the eyelid detection device 10 is connected to an image capturing unit 1. Hereafter, a case in which the eyelid detection device 10 is mounted in a vehicle to detect an eyelid of a driver is shown as an example. The eyelid detection device 10 detects the upper eyelid of an eye of a driver wearing a lot of makeup on his or her eyelids, and the upper eyelid of an eye of a driver whose face has chiseled features, which are likely to cause shadows around his or her eyes, with a high degree of accuracy.

The image capturing unit 1 includes one or more cameras mounted in a vehicle cabin. As the image capturing unit 1, a camera having sensitivity in a visible light region can be used, or a camera having sensitivity in an invisible light region, such as an infrared camera, can be used. In a case in which the image capturing unit 1 employs an infrared camera or the like, an illuminating device such as an light emitting diode (LED) that emits invisible light such as infrared light is mounted in the vehicle cabin, so that invisible light is emitted toward the driver. The image capturing unit 1 captures an image of the face of the driver under control of the controlling unit 16, and outputs the captured image to the image acquiring unit 11.

The image acquiring unit 11 acquires the captured image from the image capturing unit 1 and outputs the captured image to the controlling unit 16.

The face detecting unit 12 receives the captured image, which is acquired by the image acquiring unit 11 from the image capturing unit 1, from the controlling unit 16. The face detecting unit 12 detects the face of the driver from the captured image, and outputs a result of face detection to the controlling unit 16.

The face detecting unit 12 is, for example, a classifier which is made using Haar-like detectors and a typical algorithm which is a combination of Adaboost and Cascade. Instead of the configuration in which the eyelid detection device 10 includes the face detecting unit 12, an external device such as the image capturing unit 1 may be configured to include the face detecting unit 12. In the configuration in which an external device includes the face detecting unit 12, the image acquiring unit 11 acquires a captured image and a face detection result from the face detecting unit 12 of the external device, and outputs the captured image and the face detection result to the controlling unit 16.

The face feature point detecting unit 13 receives from the controlling unit 16 both the captured image, which is acquired by the image acquiring unit 11 from the image capturing unit 1, and the face detection result detected by the face detecting unit 12. The face feature point detecting unit 13 detects outer and inner eye corners as face feature points from the position of the face on the captured image on the basis of the face detection result, and outputs a result of face feature point detection to the controlling unit 16.

The face feature point detecting unit 13 is a detector which is made using, for example, a typical algorithm such as model fitting or a method called Elastic Bunch Graph Matching. Instead of the configuration in which the eyelid detection device 10 includes the face feature point detecting unit 13, an external device such as the image capturing unit 1 may be configured to include the face feature point detecting unit 13. In the configuration in which an external device includes the face feature point detecting unit 13, the image acquiring unit 11 acquires a captured image and a face feature point detection result from the face feature point detecting unit 13 of the external device, and outputs the captured image and the face feature point detection result to the controlling unit 16.

The eye region detecting unit 14 receives from the controlling unit 16 both the captured image, which is acquired by the image acquiring unit 11 from the image capturing unit 1, and the face feature point detection result detected by the face feature point detecting unit 13. The eye region detecting unit 14 detects an eye region from the captured image on the basis of the positions of the outer and inner eye corners in the face feature point detection result, and outputs an eye region image to the controlling unit 16. The eye region includes an upper eyelid area and an eye area. The eye area includes both an area of the white of the eye and an area of the iris. Because a well-known technique can be simply used as a method of detecting an eye region on the basis of the positions of outer and inner eye corners, an explanation of the method is omitted.

The upper eyelid detecting unit 15 receives the image of the eye region detected by the eye region detecting unit 14 from the controlling unit 16. The upper eyelid detecting unit 15 divides the eye region into a plurality of areas, and detects, for each of the divided areas, a boundary between the upper eyelid area and the eye area on the basis of the pattern of arrangement of the intensity values of the pixels aligned in the divided area. The upper eyelid detecting unit 15 connects the boundaries, each being detected for one of the divided areas, to determine a line of the upper eyelid, and then outputs the line to the controlling unit 16.

The controlling unit 16 controls the operations of the image capturing unit 1 and the eyelid detection device 10. Specifically, the controlling unit 16 instructs the image capturing unit 1 to capture an image of the driver. Furthermore, the controlling unit 16 provides an instruction for the image acquiring unit 11, the face detecting unit 12, the face feature point detecting unit 13, the eye region detecting unit 14, and the upper eyelid detecting unit 15 in the eyelid detection device 10, to control the timings of their operations and control the transfer of information.

Figure 2A:
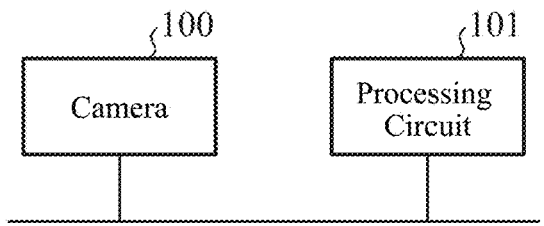
FIGS. 2A and 2B are diagrams each showing a hardware configuration example of the eyelid detection device according to Embodiment 1 of the present disclosure.
Figure 2B:
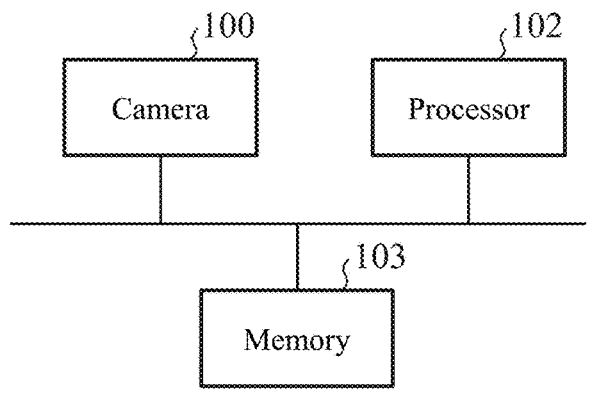

FIGS. 2A and 2B are illustrations each showing an example of a hardware configuration of the eyelid detection device 10 according to Embodiment 1 of the present disclosure. The image capturing unit 1 is a camera 100. Each of the functions of the image acquiring unit 11, the face detecting unit 12, the face feature point detecting unit 13, the eye region detecting unit 14, the upper eyelid detecting unit 15, and the controlling unit 16 in the eyelid detection device 10 is implemented by one or more processing circuits. More specifically, the eyelid detection device 10 includes a processing circuit for implementing each of the above-mentioned functions. The processing circuit can be a processing circuit 101 provided as hardware for exclusive use, or can be a processor 102 that executes a program stored in a memory 103.

As shown in FIG. 2A, in the case in which the processing circuit is hardware for exclusive use, the processing circuit 101 is, for example, a single circuit, a composite circuit, a programmable processor, a parallel programmable processor, an Application Specific Integrated Circuit (ASIC), an Field Programmable Gate Array (FPGA), or a combination of these circuits. The functions of the image acquiring unit 11, the face detecting unit 12, the face feature point detecting unit 13, the eye region detecting unit 14, the upper eyelid detecting unit 15, and the controlling unit 16 can be implemented by a plurality of processing circuits 101, or the functions of the units can be implemented collectively by a single processing circuit 101.

The camera 100 and the processing circuit 101 are connected via a bus or the like, and can perform the transfer of information between them.

As shown in FIG. 2B, in the case in which the processing circuit is a processor 102, each of the functions of the image acquiring unit 11, the face detecting unit 12, the face feature point detecting unit 13, the eye region detecting unit 14, the upper eyelid detecting unit 15, and the controlling unit 16 is implemented by software, firmware, or a combination of software and firmware. The software or the firmware is described as a program and the program is stored in the memory 103. The processor 102 implements the function of each of the units by reading and executing a program stored in the memory 103. More specifically, the eyelid detection device 10 includes the memory 103 for storing a program which, when executed by the processor 102, results in performance of the steps shown in flow charts, including FIG. 3, to be described later. Thus, the program can be seen as causing a computer to perform procedures or methods of the image acquiring unit 11, the face detecting unit 12, the face feature point detecting unit 13, the eye region detecting unit 14, the upper eyelid detecting unit 15, and the controlling unit 16.

Here, the processor 102 is a Central Processing Unit (CPU), a processing device, an arithmetic device, a microprocessor, a microcomputer, or the like.

The memory 103 can be a non-volatile or volatile semiconductor memory such as a Random Access Memory (RAM), a Read Only Memory (ROM), an Erasable Programmable ROM (EPROM), or a flash memory, can be a magnetic disk such as a hard disk or a flexible disk, or can be an optical disc such as a CD (Compact Disc) or a DVD (Digital Versatile Disc).

The camera 100, the processor 102, and the memory 103 are connected via a bus or the like, and can perform the transfer of information among them.

Some of the functions of the image acquiring unit 11, the face detecting unit 12, the face feature point detecting unit 13, the eye region detecting unit 14, the upper eyelid detecting unit 15, and the controlling unit 16 can be implemented by hardware for exclusive use, and some of the functions can be implemented by software or firmware. In this way, the processing circuit in the eyelid detection device 10 can implement each of the above-mentioned functions by using hardware, software, firmware, or a combination of hardware, software, and firmware.

Figure 3:
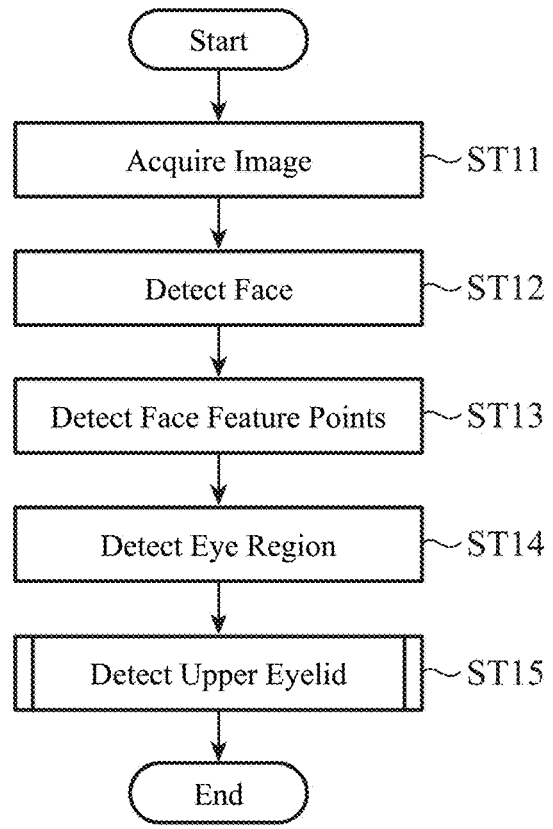
FIG. 3 is a flow chart showing an example of the operation of the eyelid detection device according to Embodiment 1 of the present disclosure.

FIG. 3 is a flow chart showing an example of the operation of the eyelid detection device 10 according to Embodiment 1 of the present disclosure. The eyelid detection device 10 repeatedly performs processing of the flow chart shown in FIG. 3. In the following explanation, an explanation of the operation of the controlling unit 16 is omitted.

At step ST11, the image acquiring unit 11 acquires a captured image of the driver of the vehicle, the image being captured by the image capturing unit 1.

At step ST12, the face detecting unit 12 detects the position of the face from the captured image.

At step ST13, the face feature point detecting unit 13 detects the positions of outer and inner eye corners from the detected face position on the captured image.

At step ST14, the eye region detecting unit 14 detects an eye region including an upper eyelid area and an eye area from the captured image on the basis of the positions of the outer and inner eye corners.

At step ST15, the upper eyelid detecting unit 15 detects an upper eyelid which is the boundary between the upper eyelid area and the eye area from the eye region.

However, in the case in which an external device includes the face detecting unit 12 and the face feature point detecting unit 13 as mentioned above, the steps ST11 to ST13 are unnecessary.

Figure 4:
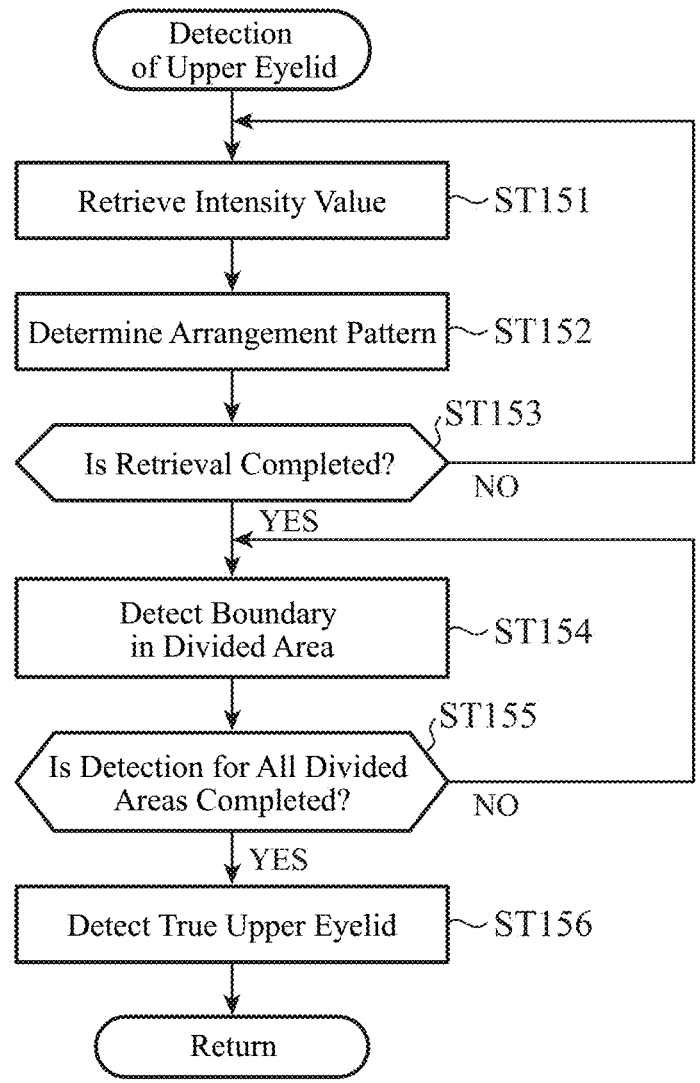
FIG. 4 is a detailed flow chart of a process at step ST15 of FIG. 3.

FIG. 4 is a detailed flow chart of the process at step ST15 of FIG. 3.

At step ST151, the upper eyelid detecting unit 15 divides the eye region into a plurality of divided areas. The upper eyelid detecting unit 15 then retrieves intensity values of all the pixels in the eye region.

Figure 5:
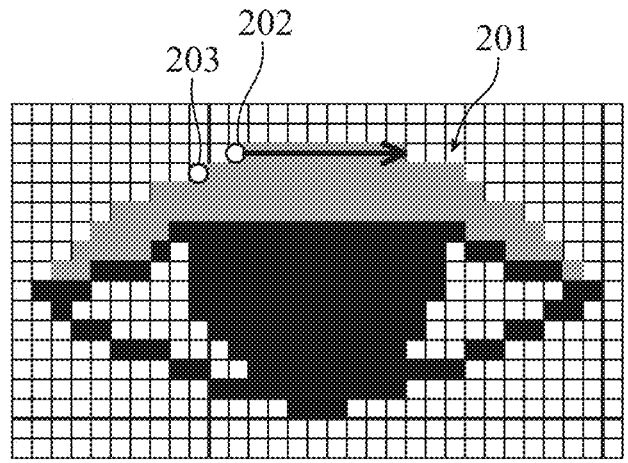
FIG. 5 is an example of an image of an eye region detected by an eye region detecting unit of the eyelid detection device according to Embodiment 1 of the present disclosure.

FIG. 5 is an example of an image of the eye region 201 detected by the eye region detecting unit 14. In this example, the upper eyelid detecting unit 15 defines the uppermost and leftmost pixel of the eye region 201 as an intensity value retrieval start position 202, and retrieves the intensity value of each pixel from the intensity value retrieval start position 202 along a horizontal direction. After that, the upper eyelid detecting unit 15 retrieves the intensity value of each pixel along the horizontal direction from an intensity value retrieval start position 203 at the leftmost end of the row just below the row retrieved above. In this way, the upper eyelid detecting unit 15 retrieves the intensity values of all the pixels in all the rows of the eye region 201. Here, the pixels of the row in the horizontal direction including the intensity value retrieval start position 202 correspond to one divided area, and the pixels of the row in the horizontal direction including the intensity value retrieval start position 203 correspond to one divided area.

Although the upper eyelid detecting unit 15 divides the eye region 201 along the horizontal direction, the manner is a non-limiting feature; the upper eyelid detecting unit may divide the eye region along a direction such as a vertical direction or a direction of a circular arc. In the case in which the eye region 201 is divided along the horizontal direction, each divided area refers to a horizontal area connecting from a pixel at the right end to a pixel at the left end of the eye region 201. Furthermore, for example, in the case in which the eye region 201 is divided along the vertical direction, each divided area is a vertical area connecting from the pixel at the upper end of the eye region 201 to the pixel at the lower end of the eye region. Furthermore, for example, in the case in which the eye region 201 is divided along a direction of an upwardly-convex circular arc, each divided area is an area extending in a direction of a circular arc and connecting from the pixel at the right end of the eye region 201 to the pixel at the left end of the eye region. In this way, each of the divided areas is an area connecting from an end of the eye region 201 to an opposite end of the eye region.

At step ST152, the upper eyelid detecting unit 15 compares the intensity value of each pixel with the intensity value of another pixel which is adjacent to the pixel with respect to the horizontal direction, to determine an arrangement pattern of the intensity values. To determine an arrangement pattern, the upper eyelid detecting unit 15 uses both a first threshold and a second threshold.

For example, the eyelid detection device 10 detects an iris from the captured image by using a typical algorithm such as Hough transformation during the calibration thereof, and sets up first and second thresholds on the basis of the intensity value of a pixel in the iris. The first threshold is a value for determining the iris, and a pixel having an intensity value less than the first threshold has a high possibility of being included in the iris. The second threshold is a value for determining the white of the eye, and a pixel having an intensity value equal to or greater than the second threshold has a high possibility of being included in the white of the eye. A pixel having an intensity value equal to or greater than the first threshold and less than the second threshold has a high possibility of being included in neither the iris nor the white of the eye, but reflecting makeup or a shadow. The second threshold is a value greater than the first threshold.

The timing at which the eyelid detection device 10 performs the calibration does not matter. For example, the eyelid detection device 10 performs the calibration within several seconds during which the driver sits on the seat and directs his or her face toward a specific direction immediately after the engine of the vehicle is started. By performing the calibration at this timing, information about the eye of the driver in a normal state can be acquired.

Figure 6A:
FIGS. 6A and 6B are illustrations used to explain a method of determining an arrangement pattern, the method being used by an upper eyelid detecting unit of the eyelid detection device according to the Embodiment 1 of the present disclosure.
Figure 6B:
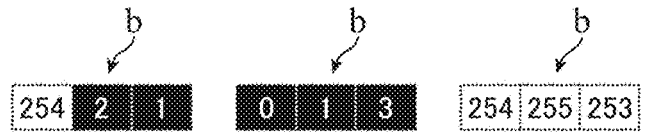

FIGS. 6A and 6B are illustrations for explanation of a method of determining an arrangement pattern a or b, the method being used by the upper eyelid detecting unit 15. The arrangement pattern a is one in which pixels each having an intensity value equal to or greater than the first threshold and less than the second threshold are continuously arranged. This arrangement pattern is used for determining the upper eyelid area in the eye region 201.

The arrangement pattern b includes an arrangement pattern in which a pixel having an intensity value less than the first threshold and a pixel having an intensity value equal to or greater than the second threshold are continuously arranged, an arrangement pattern in which pixels each having an intensity value less than the first threshold are continuously arranged, and an arrangement pattern in which pixels each having an intensity value equal to or greater than the second threshold are continuously arranged. The arrangement pattern b is used to determine the eye area in the eye region 201.

With reference to FIG. 6A, three continuously-arranged pixels on the left-hand side of the page have intensity values of "53", "52", and "56", and all of the intensity values are equal to or greater than the first threshold and less than the second threshold. Therefore, the upper eyelid detecting unit 15 determines these three pixels as pixels involving the arrangement pattern a.

Similarly, three continuously-arranged pixels on the right-hand side of the paper of FIG. 6A have intensity values of "46", "43", and "49", and all of the intensity values are equal to or greater than the first threshold and less than the second threshold. Therefore, the upper eyelid detecting unit 15 determines these three pixels as pixels involving the arrangement pattern a.

With reference to of FIG. 6B, three continuously-arranged pixels on the left-hand side of the paper have intensity values of "254", "2", and "1", and the intensity value of "254" is equal to or greater than the second threshold and the intensity values of "2" and "1" are less than the first threshold. Therefore, the upper eyelid detecting unit 15 determines these three pixels as pixels involving the arrangement pattern b.

Three continuously-arranged pixels in the center of the paper of FIG. 6B have intensity values of "0", "1", and "3", and all of the intensity values are less than the first threshold. Therefore, the upper eyelid detecting unit 15 determines these three pixels as pixels involving the arrangement pattern b.

Three continuously-arranged pixels on the right-hand side of the page of FIG. 6B have intensity values of "254", "255", and "253", and all of the intensity values are equal to or greater than the second threshold. Therefore, the upper eyelid detecting unit 15 determines these three pixels as pixels involving the arrangement pattern b.

Although the upper eyelid detecting unit 15 determines an arrangement pattern in the horizontal direction because the eye region 201 is divided along the horizontal direction, in the case in which the eye region is divided along a direction other than the horizontal direction, the upper eyelid detecting unit can determine an arrangement pattern in the direction of the division. Further, although the upper eyelid detecting unit 15 determines the arrangement pattern a or b by setting three pixels arranged contiguously in the horizontal direction as a target, the number of target pixels is not limited to three and can be increased to four or more.

At step ST153, if the upper eyelid detecting unit 15 completes both the retrieval of the intensity values and the determination of an arrangement pattern for all the pixels in the eye region 201 ("YES" at step ST153), then it proceeds to step ST154. In contrast, if a pixel for which the retrieval of the intensity value and the determination of an arrangement pattern are not completed exists ("NO" at step ST153), then the upper eyelid detecting unit 15 returns to step ST151.

At step ST154, the upper eyelid detecting unit 15 may detect, for each of the divided areas, a boundary between the upper eyelid area and the eye area on the basis of one or more arrangement patterns in a divided area.

Figure 7A:
FIGS. 7A, 7B, and 7C are illustrations used to explain a method of detecting the boundary between an upper eyelid area and an eye area, the method being used by the upper eyelid detecting unit of the eyelid detection device according to Embodiment 1 of the present disclosure.
Figure 7B:
Figure 7C:
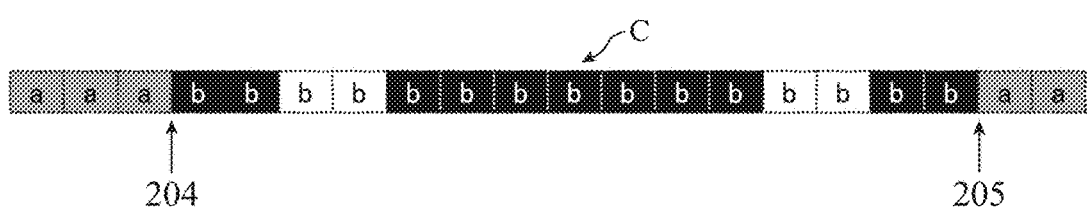

FIGS. 7A, 7B, and 7C are illustrations that are used to explain a method of detecting a boundary between the upper eyelid area and the eye area, the method being used by the upper eyelid detecting unit 15. The upper eyelid detecting unit 15 classifies each of the divided areas into divided areas A, B, and C. Only arrangement patterns a exist in the divided area A, as shown in FIG. 7A. Only arrangement patterns b exist in the divided area B, as shown in FIG. 7B. Arrangement patterns a and b coexist in the divided area C, as shown in FIG. 7C. Next, the upper eyelid detecting unit 15 detects boundaries 204 and 205, each existing between arrangement patterns a and b in the divided area C. The boundaries 204 and 205 between arrangement patterns a and b are in the boundary between the upper eyelid area and the eye area. On the other hand, because there are no boundaries in the divided areas A and B, the upper eyelid detecting unit 15 does not perform the boundary detection process on the divided areas A and B.

Figure 8:
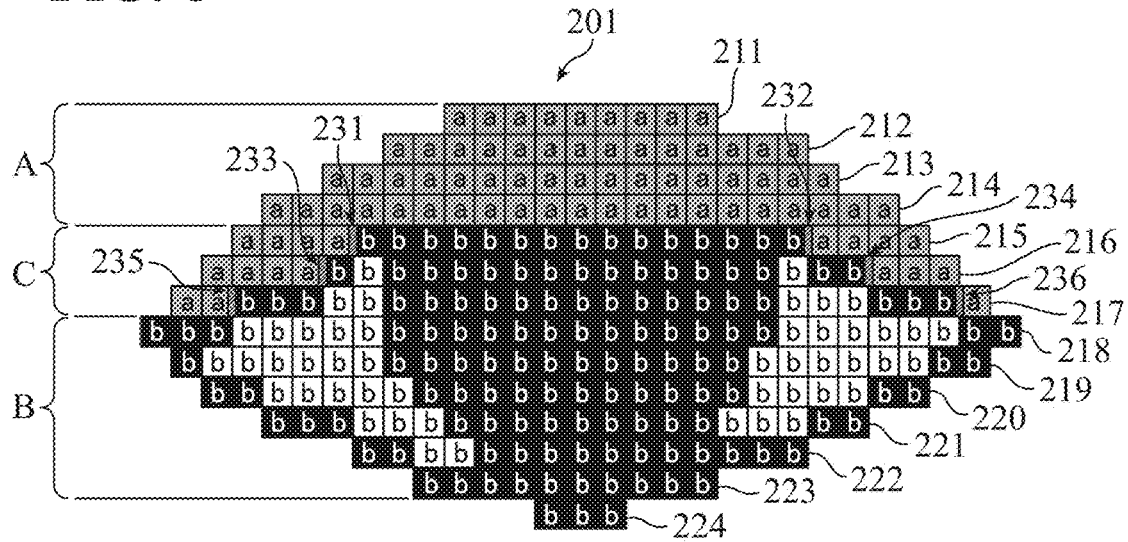
FIG. 8 is an illustration showing arrangement patterns and the boundary in the eye region of FIG. 5.

FIG. 8 is an illustration showing the arrangement patterns a and b and boundaries 231 to 236 in the eye region 201 of FIG. 5. Divided areas 215 to 217 out of the divided areas 211 to 224 into which the eye region 201 is divided along the horizontal direction are divided areas C in each of which arrangement patterns a and b coexist. The upper eyelid detecting unit 15 detects the boundaries 231 to 236 from the divided areas 215 to 217.

At step T155, if the upper eyelid detecting unit 15 completes the detection of a boundary for all the divided areas ("YES" at step ST155), then it proceeds to step ST156. In contrast, if a divided area for which the boundary detection is not completed exists ("NO" at step ST155), then the upper eyelid detecting unit 15 returns to step ST154.

At step ST156, the upper eyelid detecting unit 15 connects the boundary detected for each divided area to determine an upper eyelid.

Figure 9:
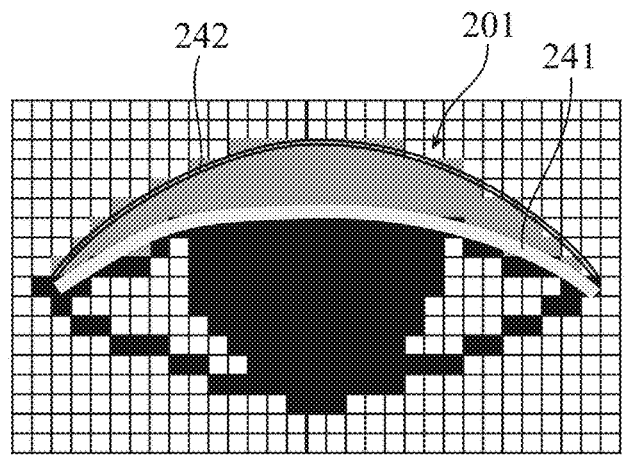
FIG. 9 is an illustration showing the upper eyelid in the eye region of FIG. 5.

FIG. 9 is an illustration showing the upper eyelid 241 in the eye region 201 of FIG. 5. The upper eyelid detecting unit 15 connects the boundaries 231 to 236 detected from the divided areas 215 to 217 of FIG. 8, to determine the upper eyelid 241. At that time, the upper eyelid detecting unit 15 determines the line of the upper eyelid 241 by means of, for example, curve fitting using both the positions of the boundaries 231 to 236 and the positions of the outer and inner eye corners detected by the face feature point detecting unit 13. Note that the area above the line of the upper eyelid 241, i.e., the divided area A in FIG. 8 is makeup or a shadow. Although in the conventional technology explained previously, a line shown by a double line, i.e., an upper line of makeup or a shadow is detected erroneously as an upper eyelid 242, an upper line of makeup or a shadow is not detected erroneously as an upper eyelid in Embodiment 1.

As explained above, the eyelid detection device 10 according to Embodiment 1 is configured so as to include: the face feature point detecting unit 13 for detecting outer and inner eye corners as face feature points from a captured image; the eye region detecting unit 14 for detecting an eye region including both an upper eyelid area and an eye area from the captured image on the basis of the face feature points; and the upper eyelid detecting unit 15 for, for each of a plurality of divided areas into which the eye region is divided, detecting the boundary between the upper eyelid area and the eye area on the basis of the pattern of arrangement of the intensity values of pixels aligned in a divided area, and for connecting the boundaries each detected in the divided area to determine an upper eyelid. As a result, an upper eyelid of a person having makeup or a shadow around his or her eyes can be detected with a high degree of accuracy.

Furthermore, the upper eyelid detecting unit 15 of Embodiment 1 is configured so as to, for each of the divided areas, use the first threshold and the second threshold greater than the first threshold, to determine, as belonging to the upper eyelid area, an arrangement pattern a in which pixels each having an intensity value equal to or greater than the first threshold and less than the second threshold are continuously arranged, and determine, as belonging to the eye area, an arrangement pattern b in which a pixel having an intensity value less than the first threshold and a pixel having an intensity value equal to or greater than the second threshold are continuously arranged, in which pixels each having an intensity value less than the first threshold are continuously arranged, or in which pixels each having an intensity value equal to or greater than the second threshold are continuously arranged. As a result, the upper eyelid can be easily detected with a high degree of accuracy.

Embodiment 2

Above-explained Embodiment 1 is based on the premise that the number of upper eyelids detected by the upper eyelid detecting unit 15 is one. However, there is a possibility that a plurality of upper eyelid lines are detected by the method of Embodiment 1 if an eyeshadow is applied onto the eyelids in such a way that shading is clearly seen, if a plurality of pieces of eyeliner are applied, or if a plurality of shadows are made around the eyes. On the other hand, in Embodiment 2, if an upper eyelid detecting unit 15 detects a plurality of upper eyelids, then it determines, as a true upper eyelid, an upper eyelid that has the largest degree of change in intensity value among the plurality of upper eyelids. Hereafter, the degree of change in intensity value of an upper eyelid is referred to as edge intensity.

Figure 10:
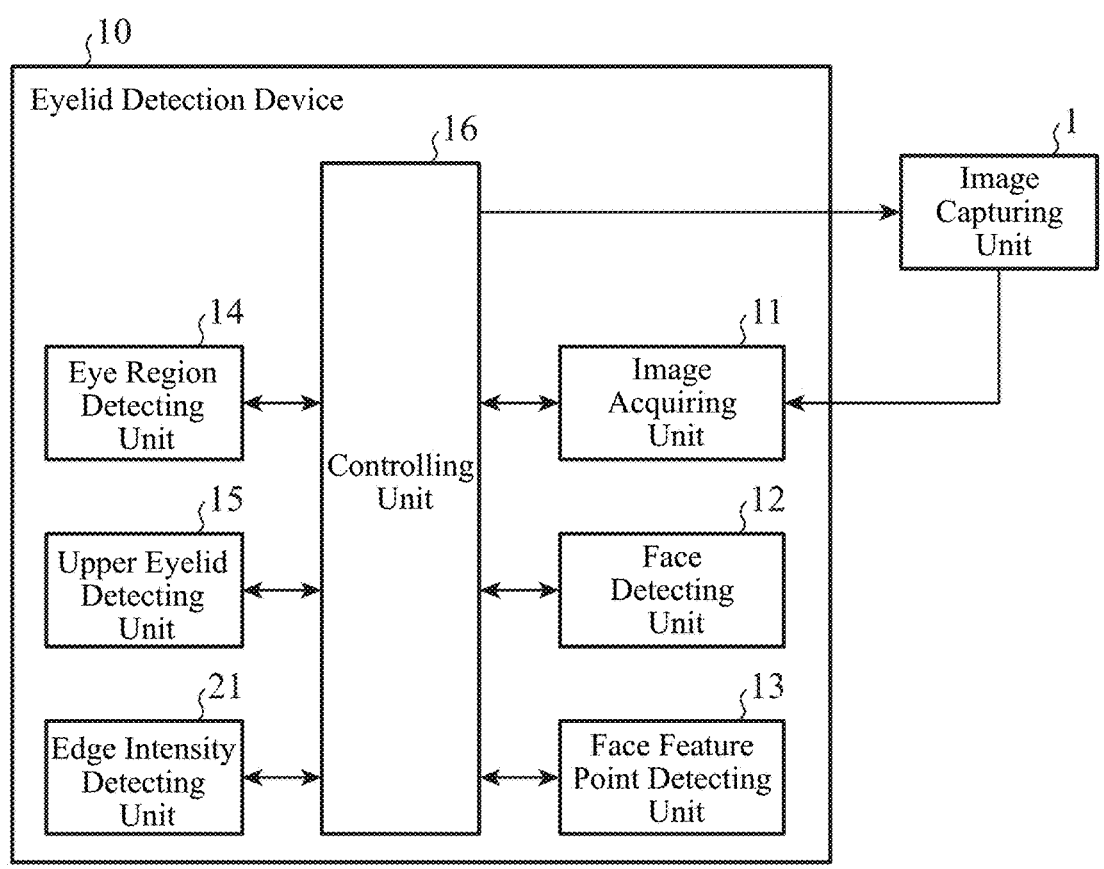
FIG. 10 is a block diagram showing a configuration example of an eyelid detection device according to Embodiment 2 of the present disclosure.

FIG. 10 is a block diagram showing a configuration example of an eyelid detection device 10 according to Embodiment 2 of the present disclosure. The eyelid detection device 10 according to Embodiment 2 has a configuration in which an edge intensity detecting unit 21 is added to the eyelid detection device 10 of Embodiment 1 shown in FIG. 1. In FIG. 10, the same components as those of FIG. 1 or like components are designated by the same reference numerals, and an explanation of the components will be omitted hereafter.

The edge intensity detecting unit 21 is implemented by the processing circuit 101 shown in FIG. 2A. Alternatively, the edge intensity detecting unit 21 is implemented by the processor 102, shown in FIG. 2B, executing a program stored in a memory 103.

Figure 11:
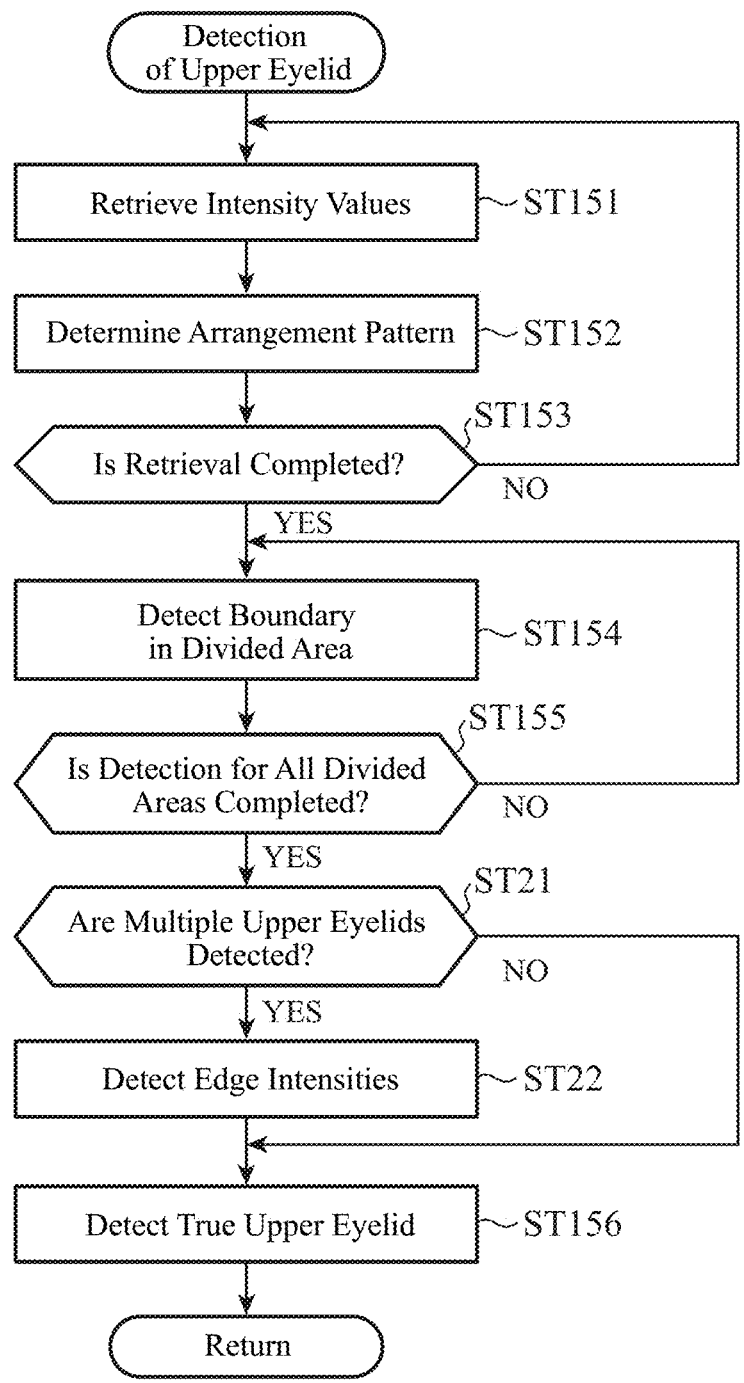
FIG. 11 is a flow chart showing an example of the operation of the eyelid detection device according to Embodiment 2 of the present disclosure.

FIG. 11 is a flowchart showing an example of the operation of the eyelid detection device 10 according to Embodiment 2 of the present disclosure. Because operations at steps ST151 to ST156 in FIG. 11 are the same as those at steps ST151 to ST156 in FIG. 4, an explanation of the operations will be omitted herein.

At step ST21, if the upper eyelid detecting unit 15 detects a plurality of upper eyelids ("YES" at step ST21), then it outputs a result of the detection of the upper eyelids to the edge intensity detecting unit 21 via a controlling unit 16 and advances to step ST22. In contrast, if the upper eyelid detecting unit 15 detects a single upper eyelid ("NO" at step ST21), then it advances to step ST156.

At step ST22, the edge intensity detecting unit 21 receives the result of the detection of the upper eyelids from the upper eyelid detecting unit 15 via the controlling unit 16. The edge intensity detecting unit 21 detects the edge intensity for each of the plurality of upper eyelids. The edge intensity detecting unit 21 outputs the detection results for edge intensity to the upper eyelid detecting unit 15 via the controlling unit 16.

At step ST156 following step ST22, the upper eyelid detecting unit 15 receives the detection results for edge intensity from the edge intensity detecting unit 21 via the controlling unit 16. An edge of an upper eyelid has higher edge intensity than an edge occurring due to either makeup such as eyeshadow or eyeliner, or a shadow around an eye. Accordingly, the upper eyelid detecting unit 15 determines, as a true upper eyelid, an upper eyelid having the highest edge intensity among the plurality of upper eyelids on the basis of the detection results for edge intensity.

Figure 12A:
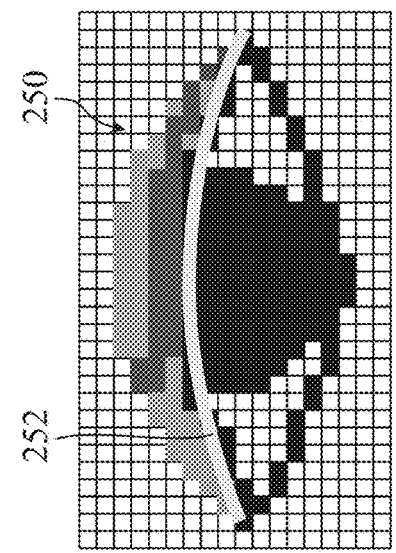
FIGS. 12A, 12B, and 12C are views used to explain a method of detecting an upper eyelid performed by the eyelid detection device according to Embodiment 2 of the present disclosure.
Figure 12B:
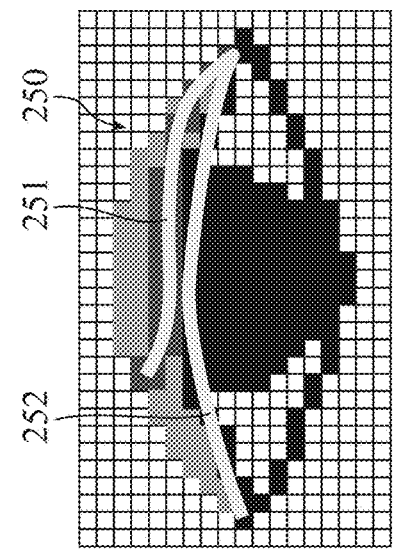
Figure 12C:
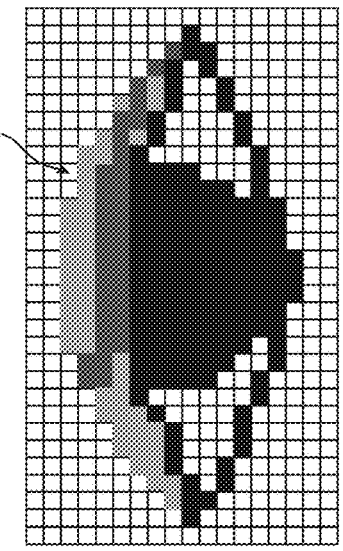

FIGS. 12A, 12B, and 12C are illustrations used to explain a method of detecting an upper eyelid, the method being used by the eyelid detection device 10 according to Embodiment 2 of the present disclosure. In an example of an image of an eye region 250 shown in FIG. 12A, eyeshadow having clear shading is applied to an upper eyelid. As shown in FIG. 12B, the upper eyelid detecting unit 15 detects two upper eyelids 251 and 252 from the eye region 250. The edge intensity detecting unit 21 detects an edge intensity on the basis of the intensity values of the upper eyelid 251 and the intensity value of each of pixels in an area surrounding the upper eyelid. Similarly, the edge intensity detecting unit 21 detects an edge intensity on the basis of the intensity values of the upper eyelid 252 and the intensity value of each of pixels in an area surrounding the upper eyelid. The edge intensity of the upper eyelid 252 is higher than that of the upper eyelid 251. Therefore, as shown in FIG. 12C, the upper eyelid detecting unit 15 determines the upper eyelid 252 as the true upper eyelid.

As explained above, the eyelid detection device 10 according to Embodiment 2 is configured to include the edge intensity detecting unit 21 for detecting the degree of change in intensity value of each of upper eyelids in response to the upper eyelid detecting unit 15 detecting the upper eyelids. The upper eyelid detecting unit 15 is configured to determine, as the true upper eyelid, an upper eyelid having the largest degree of change in intensity value detected by the edge intensity detecting unit 21 among a plurality of upper eyelids. With this configuration, an upper eyelid of a person wearing special makeup such as eyeshadow having clear shading, or a plurality of lines of eyeliner, or a person having a plurality of shadows around his or her eyes can be detected with a further high degree of accuracy.

Embodiment 3

In Embodiment 3, an eyelid detection device 10 detects a lower eyelid as well as an upper eyelid. Furthermore, the eyelid detection device 10 calculates a degree of eye openness.

Figure 13:
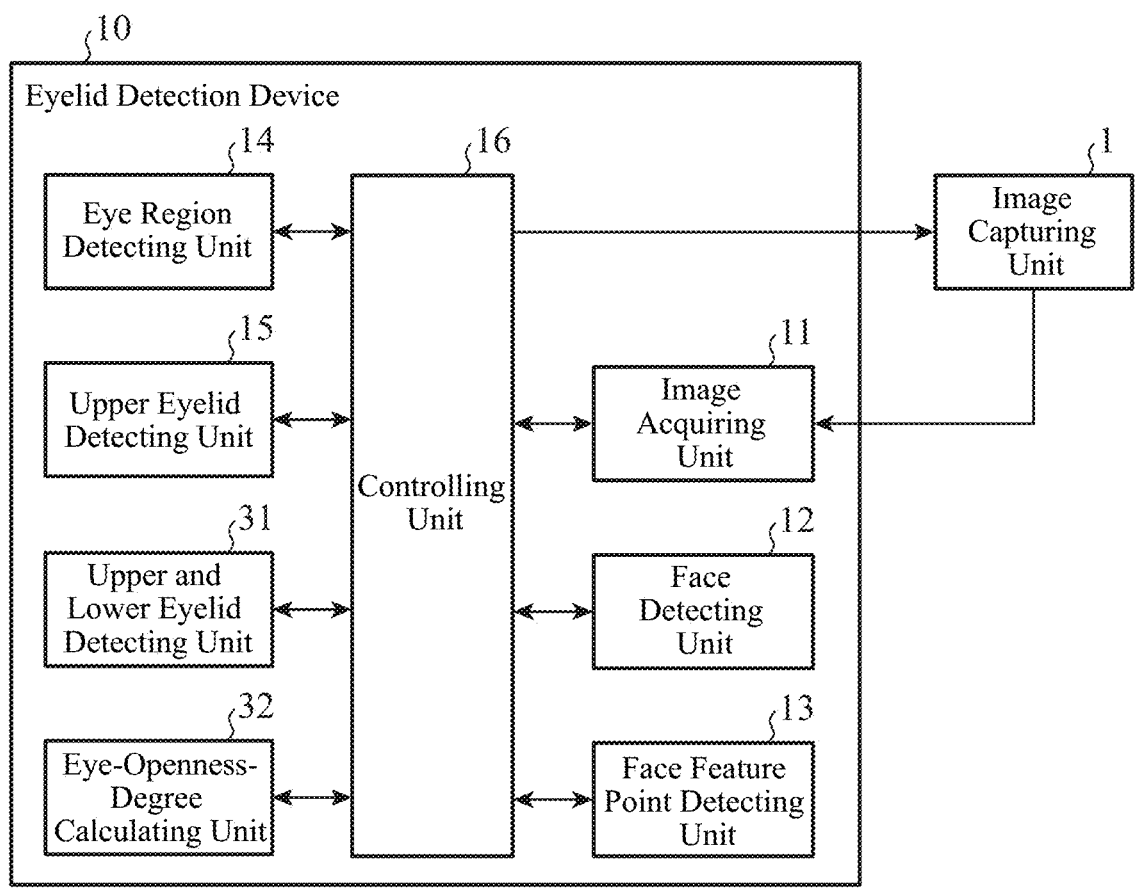
FIG. 13 is a block diagram showing a configuration example of an eyelid detection device according to Embodiment 3 of the present disclosure.

FIG. 13 is a block diagram showing a configuration example of the eyelid detection device 10 according to Embodiment 3 of the present disclosure. The eyelid detection device 10 according to Embodiment 3 is configured to include an upper and lower eyelid detecting unit 31 and an eye-openness-degree calculating unit 32, in addition to the eyelid detection device 10 of Embodiment 1 shown in FIG. 1. In FIG. 13, the same components as those of FIG. 1 or like components are designated by the same reference numerals, and an explanation of the components is omitted hereafter.

The upper and lower eyelid detecting unit 31 and the eye-openness-degree calculating unit 32 are implemented by the processing circuit 101 shown in FIG. 2A. Alternatively, the upper and lower eyelid detecting unit 31 and the eye-openness-degree calculating unit 32 may be implemented by the processor 102, shown in FIG. 2B, executing a program stored in the memory 103.

Figure 14:
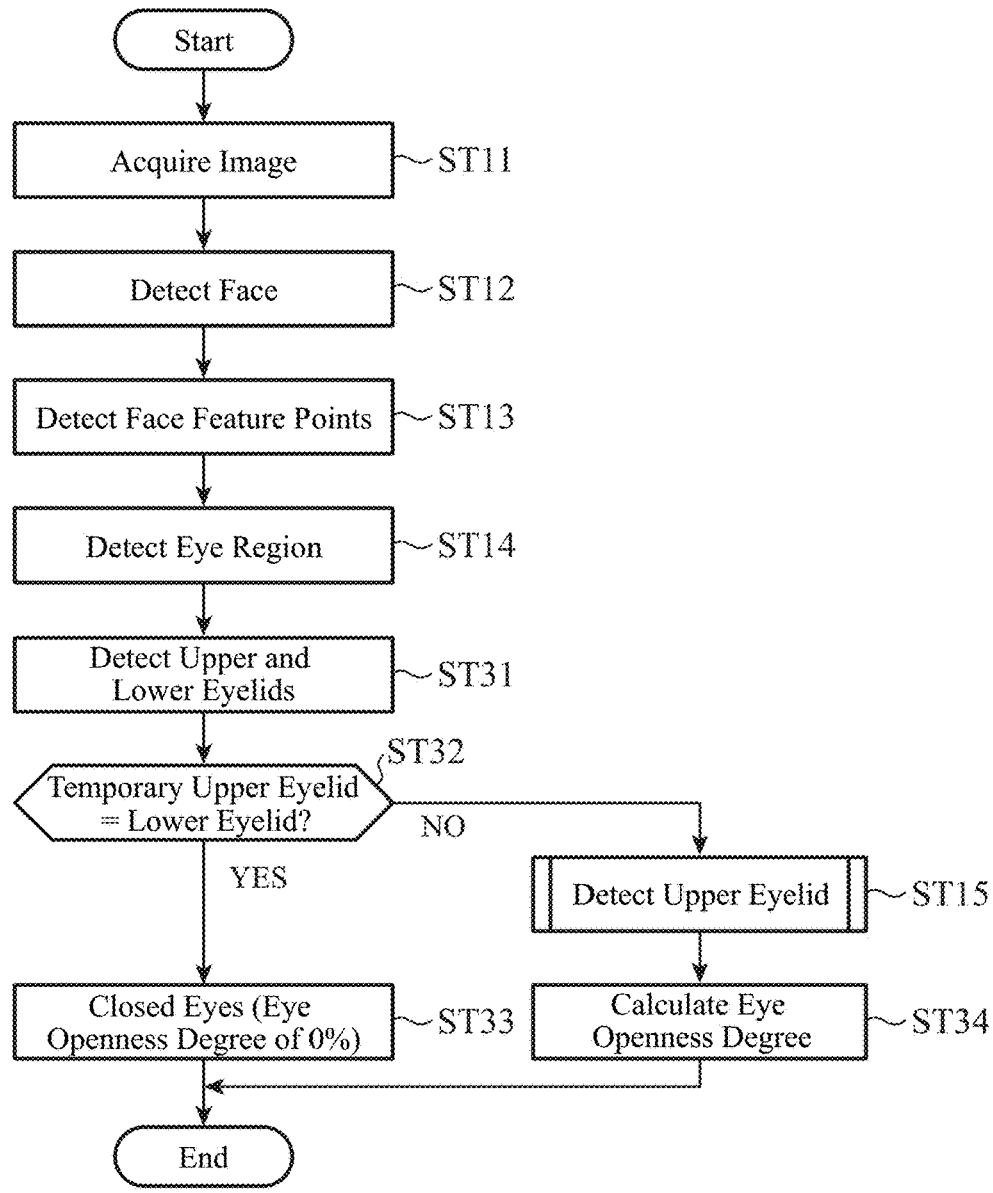
FIG. 14 is a flow chart showing an example of the operation of the eyelid detection device according to Embodiment 3 of the present disclosure.

FIG. 14 is a flowchart showing an example of the operation of the eyelid detection device 10 according to Embodiment 3 of the present disclosure. Because operations at steps ST11 to ST15 in FIG. 14 are the same as those at steps ST11 to ST15 in FIG. 3, an explanation of the operations will be omitted herein.

At step ST31, the upper and lower eyelid detecting unit 31 receives from a controlling unit 16 both a face feature point detection result detected by a face feature point detecting unit 13 and an image of an eye region detected by an eye region detecting unit 14. The upper and lower eyelid detecting unit 31 detects a temporary upper eyelid and a lower eyelid from the eye region on the basis of the positions of outer and inner eye corners in the face feature point detection result. The upper and lower eyelid detecting unit 31 outputs a result of the detection of the temporary upper eyelid and the lower eyelid to the controlling unit 16.

The upper and lower eyelid detecting unit 31 detects an edge from the eye region using, for example, a typical image processing filter such as the Sobel filter or Laplacian filter. Next, the upper and lower eyelid detecting unit 31 detects curves using the positions of the outer and inner eye corners and a result of the edge detection. Two detected curves are regarded as the lines of a temporary upper eyelid and a lower eyelid. In detecting the curves, a typical algorithm such as Hough transformation is used.

At step ST32, the eye-openness-degree calculating unit 32 receives from the controlling unit 16 the result of the detection of the temporary upper eyelid and the lower eyelid detected by the upper and lower eyelid detecting unit 31. If the temporary upper eyelid and the lower eyelid match ("YES" at step ST32), then the eye-openness-degree calculating unit 32 proceeds to step ST33. In contrast, if the temporary upper eyelid and the lower eyelid do not match ("NO" at step ST32), then the eye-openness-degree calculating unit 32 notifies the controlling unit 16 thereof. In response to receiving the notification, the controlling unit 16 proceeds to step ST15 and further to step ST34.

At step ST33, the eye-openness-degree calculating unit 32 determines that the eyes of a driver are closed because the temporary upper eyelid and the lower eyelid which are detected by the upper and lower eyelid detecting unit 31 match. The eye-openness-degree calculating unit 32 calculates the degree of eye openness as 0%.

Note that if the temporary upper eyelid and the lower eyelid match only the divided area A shown in FIG. 7A exists in the eye region.

At step ST34 following step ST15, the eye-openness-degree calculating unit 32 determines that the eyes of the driver are open and calculates the degree of eye openness because the temporary upper eyelid and the lower eyelid which are detected by the upper and lower eyelid detecting unit 31 do not match. At the time of the calculation of the degree of eye openness, the eye-openness-degree calculating unit 32 uses the upper eyelid detected at step ST15 by assuming a case in which makeup is thickly applied around the eyes of the driver or a case in which there is a shadow around the eyes of the driver.

Figure 15:
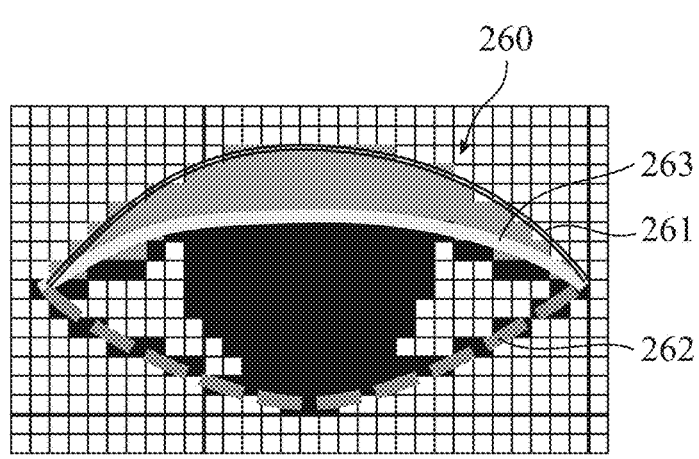
FIG. 15 is a view used to explain a method of detecting upper and lower eyelids performed by an upper and lower eyelid detecting unit of the eyelid detection device according to Embodiment 3 of the present disclosure.

FIG. 15 is an illustration used to explain a method, performed by the upper and lower eyelid detecting unit 31, of detecting upper and lower eyelids. In an example of an image of the eye region 260 shown in FIG. 15, a true upper eyelid 263 and a lower eyelid 262 are objects to be detected. However, an area of makeup or a shadow exists above the true upper eyelid 263. Thus, when performing edge detection and curve detection, the upper and lower eyelid detecting unit 31 erroneously detects an edge of the area of makeup or a shadow as a temporary upper eyelid 261. Accordingly, the eye-openness-degree calculating unit 32 calculates the degree of eye openness by using, instead of the temporary upper eyelid 261 detected by the upper and lower eyelid detecting unit 31, the true upper eyelid 263 detected by the upper eyelid detecting unit 15.

For example, the eye-openness-degree calculating unit 32 uses information about the eyes of the driver in a normal state, the information being acquired by the eyelid detection device 10 during the calibration thereof, to calculate a distance in a vertical direction of the eye area in the normal state, to define this distance as a reference distance with an degree of eye openness of 100%.

The eye-openness-degree calculating unit 32 receives both a result of the detection of the lower eyelid detected by the upper and lower eyelid detecting unit 31, and a result of the detection of the upper eyelid detected by the upper eyelid detecting unit 15, via the controlling unit 16. The eye-openness-degree calculating unit 32 calculates a distance between the lower eyelid and the upper eyelid, and compares the distance calculated thereby with the reference distance to calculate the degree of eye openness. It is assumed that at step ST34, the eye-openness-degree calculating unit 32 calculates the degree of eye openness ranging from 1% to 100%.

Note that, if the degree of eye openness ranges from 1% to 99%, all the divided areas A, B, and C shown in FIGS. 7A, 7B, and 7C exist in the eye region. In contrast, if the degree of eye openness is 100%, only the divided area B shown in FIG. 7B exists in the eye region.

Figure 16A:
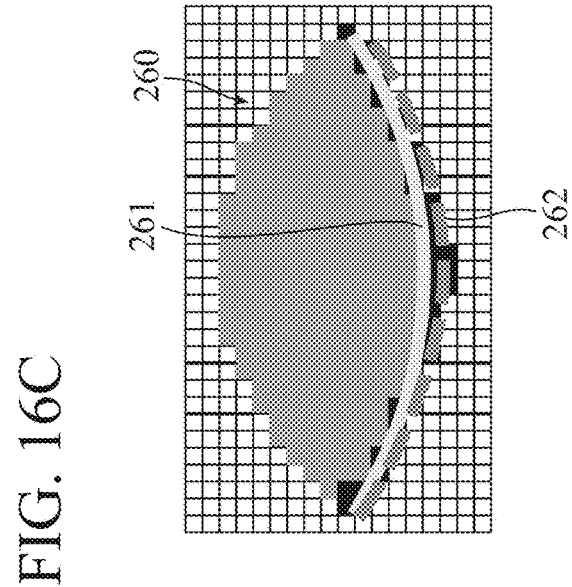
FIGS. 16A, 16B, and 16C are illustrations used to explain a method of calculating a degree of eye openness performed by an eye-openness-degree calculating unit of the eyelid detection device according to Embodiment 3 of the present disclosure.
Figure 16B:
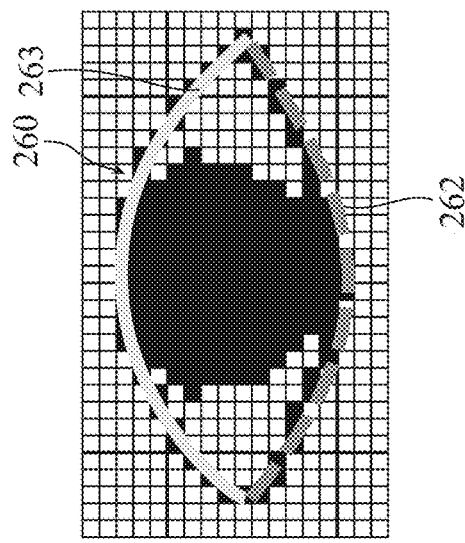
Figure 16C:
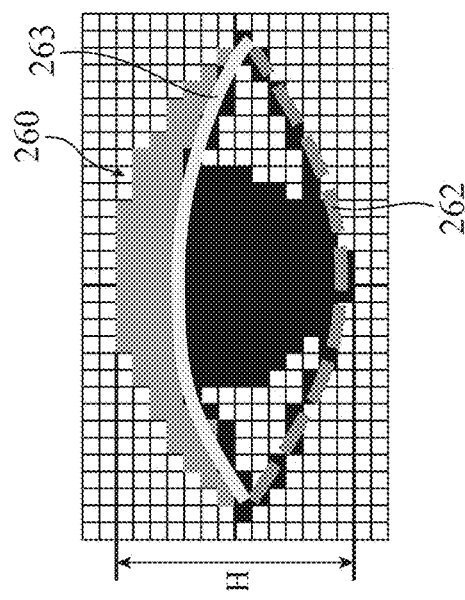

FIGS. 16A, 16B and 16C are illustrations used to explain a method, performed by the eye-openness-degree calculating unit 32, of calculating the degree of eye openness. As shown in FIG. 16A, if all the divided areas A, B and C, shown in FIGS. 7A, 7B and 7C, exist in the eye region 260, the upper eyelid detecting unit 15 detects the boundary between arrangement patterns a and b in the divided area C as the true upper eyelid 263. The eye-openness-degree calculating unit 32 calculates a degree of eye openness on the basis of both the reference distance H and the distance between the true upper eyelid 263 and the lower eyelid 262. In FIG. 16A, the degree of eye openness is 65%.

If the reference distance H is equal to the distance between the true upper eyelid 263 and the lower eyelid 262, as shown in FIG. 16B, the eye-openness-degree calculating unit 32 calculates the degree of eye openness as 100%. Instead of calculating the degree of eye openness as 100% for the case in which the reference distance H is equal to the distance between the true upper eyelid 263 and the lower eyelid 262, the eye-openness-degree calculating unit 32 may calculate the degree of eye openness as 100% if only the divided area B exists in the eye region 260.

If the temporary upper eyelid 261 and the lower eyelid 262 match, as shown in FIG. 16C, the eye-openness-degree calculating unit 32 calculates the degree of eye openness as 0%. Instead of calculating the degree of eye openness as 0% for the case in which the temporary upper eyelid 261 and the lower eyelid 262 match, the eye-openness-degree calculating unit 32 may calculate the degree of eye openness as 0% if only the divided area A exists in the eye region 260.

As explained above, the eyelid detection device 10 according to Embodiment 3 is configured so as to include the upper and lower eyelid detecting unit 31 for detecting a temporary upper eyelid and a lower eyelid from the eye region on the basis of the face feature points. The upper eyelid detecting unit 15 is configured so as to determine the upper eyelid detected by the upper eyelid detecting unit 15 as the true upper eyelid if the temporary upper eyelid and the lower eyelid which are detected by the upper and lower eyelid detecting unit 31 do not match. As a result, an upper eyelid of a person having makeup or a shadow around his or her eyes, not to mention a person having a normal appearance around his or her eyes, can also be detected with a high degree of accuracy.

Furthermore, the eyelid detection device 10 according to Embodiment 3 is configured so as to include the eye-openness-degree calculating unit 32 that calculates the degree of eye openness by using both the true upper eyelid detected by the upper eyelid detecting unit 15 and the lower eyelid detected by the upper and lower eyelid detecting unit 31. As a result, because an upper eyelid of a person having makeup or a shadow around his or her eyes can be detected with a high degree of accuracy, the degree of eye openness of such a person can also be calculated with a high degree of accuracy.

The eyelid detection device 10 according to Embodiment 3 can include the edge intensity detecting unit 21 in Embodiment 2. With this configuration, an upper eyelid of a person wearing special makeup such as eyeshadow having clear shading, or multiple lines of eyeliner, or a person having multiple of shadows around his or her eyes, not to mention a person having a normal appearance around his or her eyes, can also be detected with a high degree of accuracy. Furthermore, the degree of eye openness of such a person can also be calculated with a high degree of accuracy.

Embodiment 4

In Embodiment 4, drowsiness is determined using a result of the calculation of a degree of eye openness.

Figure 17:
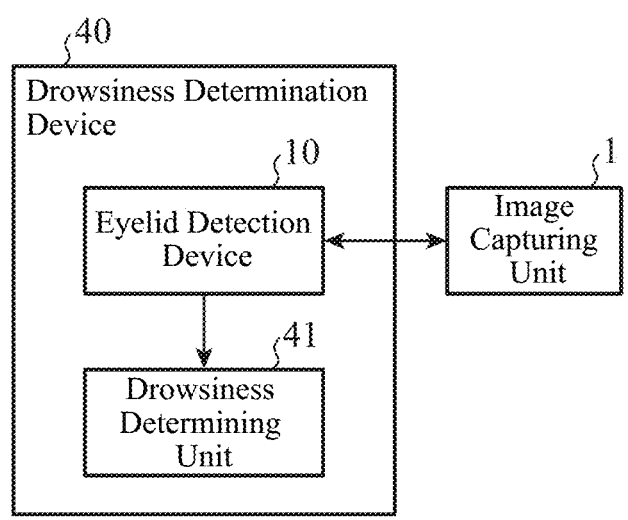
FIG. 17 is a block diagram showing a configuration example of a drowsiness determination device according to Embodiment 4 of the present disclosure.

FIG. 17 is a block diagram showing a configuration example of a drowsiness determination device 40 according to Embodiment 4 of the present disclosure. The drowsiness determination device 40 shown in FIG. 17 includes the eyelid detection device 10 according to Embodiment 3, and a drowsiness determining unit 41.

The drowsiness determining unit 41 is implemented by the processing circuit 101 shown in FIG. 2A. Alternatively, the drowsiness determining unit 41 is implemented by the processor 102, shown in FIG. 2B, executing a program stored in a memory 103.

The drowsiness determining unit 41 receives a result of the calculation of an degree of eye openness from the eye-openness-degree calculating unit 32 of the eyelid detection device 10 according to Embodiment 3. The drowsiness determining unit 41 determines whether or not the driver is drowsing on the basis of the degree of eye openness calculation result. For example, in the event that a closed eye state lasts for a predetermined time period (e.g., several seconds), the drowsiness determining unit 41 determines that the driver is drowsing.

As explained above, the drowsiness determination device 40 according to Embodiment 4 is configured so as to include the eyelid detection device 10 of Embodiment 3, and the drowsiness determining unit 41 for determining a drowsy state on the basis of the degree of eye openness calculated by the eyelid detection device 10. With this configuration, because an upper eyelid and the degree of eye openness of a person having makeup or a shadow around his or her eyes can be detected with a high degree of accuracy, the drowsiness of such a person can be determined with a high degree of accuracy.

Although in Embodiments 1 to 4, examples in which the image capturing unit 1, the eyelid detection device 10, and the drowsiness determination device 40 are mounted in the vehicle are shown, no limitation thereto is intended; for example, only the image capturing unit 1 may be mounted in the vehicle and the eyelid detection device 10 and the drowsiness determination device 40 may be provided outside the vehicle. In the latter case, for example, the image capturing unit 1 inside the vehicle, and the eyelid detection device 10 and the drowsiness determination device 40 outside the vehicle can transfer information between them via wireless communications. The eyelid detection device 10 and the drowsiness determination device 40 receive an image captured by the image capturing unit via wireless communications, detect an upper eyelid, calculate an degree of eye openness, determine drowsiness, and transmit a result of the determination to a vehicle-mounted device, such as a driver monitoring device, via wireless communications.

It is to be understood that free combinations of embodiments, modifications to any components in the embodiments, or omissions of any components may be made within the scope of the invention.

Furthermore, a person who is an object of the eyelid detection device 10 and the drowsiness determination device 40, explained in the embodiments of the present disclosure, is not limited to the driver of a vehicle; he or she may be a driver or pilot of another movable vehicle, including a railway train, a ship and an airplane. It can be expected that a driver monitoring device operates properly in a variety of use cases for drivers, such as persons of various genders and persons of various races, by using the eyelid detection device 10 and the drowsiness determination device 40 to the driver monitoring device.

INDUSTRIAL APPLICABILITY

Because the eyelid detection device and the drowsiness determination device according to the present disclosure are configured so as to detect an upper eyelid with a high degree of accuracy, the eyelid detection device and the drowsiness determination device are suitable for use in a driver monitoring device that monitors the state of the driver, and so on.

REFERENCE SIGNS LIST 1 image capturing unit; 10 eyelid detection device; 11 image acquiring unit; 12 face detecting unit; 13 face feature point detecting unit; 14 eye region detecting unit; 15 upper eyelid detecting unit; 16 controlling unit; 21 edge intensity detecting unit; 31 upper and lower eyelid detecting unit; 32 eye-openness-degree calculating unit; 40 drowsiness determination device; 41 drowsiness determining unit; 100 camera; 101 processing circuit; 102 processor; 103 memory; 201, 250, 260 eye region; 202, 203 intensity value retrieval start position; 204, 205, 231 to 236 boundary; 211 to 224 divided area; 241, 251, 252 upper eyelid; 242 erroneously-detected upper eyelid; 261 temporary upper eyelid; 262 lower eyelid; and 263 true upper eyelid.

The invention claimed is:

1. An eyelid detection device comprising:
   processing circuitry
   to detect outer and inner eye corners as face feature points from a captured image;
   to detect an eye region including both an upper eyelid area and an eye area from the captured image on a basis of the face feature points; and
   to detect, for each of a plurality of divided areas into which the eye region is divided, a boundary between the upper eyelid area and the eye area on a basis of a pattern of arrangement of intensity values of pixels aligned in a divided area, and to connect the boundaries each detected in the divided area to determine an upper eyelid,
   wherein the processing circuitry is configured to use, in one of the divided area, a first threshold and a second threshold greater than the first threshold to determine as belonging to the upper eyelid area an arrangement pattern in which pixels each having an intensity value equal to or greater than the first threshold and less than the second threshold are continuously arranged, and determine as belonging to the eye area an arrangement pattern in which a pixel having an intensity value less than the first threshold and a pixel having an intensity value equal to or greater than the second threshold are continuously arranged, in which pixels each having an intensity value less than the first threshold are continuously arranged, or in which pixels each having an intensity value equal to or greater than the second threshold are continuously arranged.

2. An eyelid detection device comprising:
   processing circuitry
   to detect outer and inner eye corners as face feature points from a captured image;
   to detect an eye region including both an upper eyelid area and an eye area from the captured image on a basis of the face feature points;
   to detect, for each of a plurality of divided areas into which the eye region is divided, a boundary between the upper eyelid area and the eye area on a basis of a pattern of arrangement of intensity values of pixels aligned in a divided area, and to connect the boundaries each detected in the divided area to determine an upper eyelid; and
   to detect a temporary upper eyelid and a lower eyelid from the eye region on a basis of the face feature points, wherein
   the processing circuitry is configured to determine that, if the detected temporary upper eyelid and the detected lower eyelid do not match, the detected upper eyelid is a true upper eyelid.

3. The eyelid detection device according to claim 2, the processing circuitry is further configured to calculate an degree of eye openness by using both the detected true upper eyelid and the detected lower eyelid detected.

4. The eyelid detection device according to claim 1, wherein each divided area is an area connecting an end of the eye region to an opposite end of the eye region.

5. The eyelid detection device according to claim 2, wherein each divided area is an area connecting an end of the eye region to an opposite end of the eye region.

6. The eyelid detection device according to claim 3, wherein each divided area is an area connecting an end of the eye region to an opposite end of the eye region.

7. The eyelid detection device according to claim 1, the processing circuitry is further configured to detect, if a plurality of upper eyelids is detected, a degree of change in intensity value for each of the plurality of upper eyelids, wherein
   to determine that an upper eyelid having a largest degree of change in intensity value detected by the processing circuitry is a true upper eyelid among the plurality of upper eyelids.

8. The eyelid detection device according to claim 2, the processing circuitry is further configured to detect, if a plurality of upper eyelids is detected, a degree of change in intensity value for each of the plurality of upper eyelids, wherein
   to determine that an upper eyelid having a largest degree of change in intensity value detected by the processing circuitry is a true upper eyelid among the plurality of upper eyelids.

9. The eyelid detection device according to claim 3, the processing circuitry is further configured to detect, if a plurality of upper eyelids is detected, a degree of change in intensity value for each of the plurality of upper eyelids, wherein
   to determine that an upper eyelid having a largest degree of change in intensity value detected by the processing circuitry is a true upper eyelid among the plurality of upper eyelids.

10. The eyelid detection device according to claim 4, the processing circuitry is further configured to detect, if a plurality of upper eyelids is detected, a degree of change in intensity value for each of the plurality of upper eyelids, wherein
    to determine that an upper eyelid having a largest degree of change in intensity value detected by the processing circuitry is a true upper eyelid among the plurality of upper eyelids.

11. The eyelid detection device according to claim 5, the processing circuitry is further configured to detect, if a plurality of upper eyelids is detected, a degree of change in intensity value for each of the plurality of upper eyelids, wherein
to determine that an upper eyelid having a largest degree of change in intensity value detected by the processing circuitry is a true upper eyelid among the plurality of upper eyelids.

12. The eyelid detection device according to claim 6, the processing circuitry is further configured to detect, if a plurality of upper eyelids is detected, a degree of change in intensity value for each of the plurality of upper eyelids, wherein
to determine that an upper eyelid having a largest degree of change in intensity value detected by the processing circuitry is a true upper eyelid among the plurality of upper eyelids.

13. A drowsiness determination device comprising:
the eyelid detection device according to claim 3; and
the processing circuitry is further configured to determine a drowsy state on a basis of the degree of eye openness calculated by the eyelid detection device.

14. An eyelid detection method comprising:
detecting outer and inner eye corners as face feature points from a captured image;
detecting an eye region including both an upper eyelid area and an eye area from the captured image on a basis of the face feature points; and
detecting for each of a plurality of divided areas into which the eye region is divided, a boundary between the upper eyelid area and the eye area on a basis of a pattern of arrangement of intensity values of pixels aligned in a divided area, and connecting the boundaries each detected in the divided area to determine an upper eyelid,
using, in one of the divided area, a first threshold and a second threshold greater than the first threshold to determine as belonging to the upper eyelid area an arrangement pattern in which pixels each having an intensity value equal to or greater than the first threshold and less than the second threshold are continuously arranged, and determine as belonging to the eye area an arrangement pattern in which a pixel having an intensity value less than the first threshold and a pixel having an intensity value equal to or greater than the second threshold are continuously arranged, in which pixels each having an intensity value less than the first threshold are continuously arranged, or in which pixels each having an intensity value equal to or greater than the second threshold are continuously arranged.

* * * * *